United States Patent
Anderson (10) Patent No.: US 8,353,939 B2
(45) Date of Patent: Jan. 15, 2013

(54) ANCHOR RETAINING MECHANISMS FOR BONE PLATES

(75) Inventor: Kent Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2373 days.

(21) Appl. No.: 11/033,586

(22) Filed: Jan. 12, 2005

(65) Prior Publication Data

US 2006/0155285 A1  Jul. 13, 2006

(51) Int. Cl.
*A61B 17/80* (2006.01)

(52) U.S. Cl. ........................................ 606/289

(58) Field of Classification Search .............. 606/60, 606/69, 70, 71, 237, 280, 289, 290
See application file for complete search history.

(56) References Cited

U.S. PATENT DOCUMENTS

| | | | |
|---|---|---|---|
| 5,364,399 A | 11/1994 | Lowery et al. | |
| 5,578,034 A | 11/1996 | Estes | |
| 5,931,838 A | 8/1999 | Vito | |
| 6,258,089 B1 | 7/2001 | Campbell et al. | |
| 6,258,092 B1 | 7/2001 | Dall | |
| 6,261,291 B1 | 7/2001 | Talaber et al. | |
| 6,331,179 B1 | 12/2001 | Freid et al. | |
| 6,402,755 B1 | 6/2002 | Pisharodi | |
| 6,454,769 B2 | 9/2002 | Wagner et al. | |
| 6,599,290 B2 | 7/2003 | Bailey et al. | |
| 6,602,255 B1 | 8/2003 | Campbell et al. | |
| 6,652,525 B1 | 11/2003 | Assaker et al. | |
| 6,663,632 B1 | 12/2003 | Frigg | |
| 6,695,846 B2 | 2/2004 | Richelsoph et al. | |
| 6,755,833 B1 | 6/2004 | Paul et al. | |
| 6,764,489 B2 | 7/2004 | Ferree | |
| 2001/0014807 A1 | 8/2001 | Wagner et al. | |
| 2002/0045896 A1 | 4/2002 | Michelson | |
| 2003/0187440 A1 | 10/2003 | Richelsoph et al. | |
| 2003/0187442 A1 | 10/2003 | Richelsoph et al. | |
| 2003/0208204 A1* | 11/2003 | Bailey et al. | 606/69 |
| 2004/0087951 A1* | 5/2004 | Khalili | 606/69 |
| 2004/0097935 A1 | 5/2004 | Richelsoph et al. | |
| 2004/0127896 A1 | 7/2004 | Lombardo et al. | |
| 2004/0127899 A1 | 7/2004 | Konieczynski et al. | |
| 2004/0127900 A1 | 7/2004 | Konieczynski et al. | |
| 2004/0127904 A1 | 7/2004 | Konieczynski et al. | |
| 2004/0260306 A1* | 12/2004 | Fallin et al. | 606/104 |
| 2005/0049593 A1 | 3/2005 | Duong et al. | |
| 2005/0283152 A1 | 12/2005 | Lindemann et al. | |

FOREIGN PATENT DOCUMENTS

| | | |
|---|---|---|
| EP | 0 903 113 A2 | 8/1998 |
| EP | 1 500 376 A1 | 7/2004 |
| FR | 2 794 963 A1 | 6/1999 |

* cited by examiner

*Primary Examiner* — Eduardo C Robert
*Assistant Examiner* — Steven Cotroneo (57) ABSTRACT

A system involving anchor retaining mechanisms for a bone plate includes a plate with at least a first hole therethrough between an upper surface and a lower surface of the plate to receive an anchor for engaging a bony segment. The system also includes a partially annular retaining member engageable to the plate and positionable in the hole of the plate to prevent anchor backout while allowing insertion of the anchor through the plate hole and removal of the anchor from the plate hole.

15 Claims, 5 Drawing Sheets

ANCHOR RETAINING MECHANISMS FOR BONE PLATES

BACKGROUND

Bone plates can be engaged to adjacent bony portions of a bone or of a bony segment to stabilize the bony portions. Anchors or fasteners, such as bone screws, can be used to engage bone plates to bony portions. To prevent the fasteners from backing out of the plate, various retaining devices have been developed for engagement or manipulation relative to the plate adjacent to or around the bone fasteners. Other retaining devices include placing a retaining cover plate over the bone plate and anchors, and thus creating a higher profile bone plate. These retaining devices block the anchors to prevent them from backing out of the plate. Measures taken to retain the screws in the bone plate and keep the screws engaged in the bony portion can improve their function and avoid problems associated with bone screw backout.

There can be some problems associated with prior retaining devices. For example, in prior retaining devices, the head of one or more of the anchors may interfere with positioning and alignment of the retaining device relative to the anchor. Prior retaining devices may not be employed with one or more of the anchors if the anchors move relative to the plate, or if multiple anchors associated with the retaining device are not at the same position relative to the plate. Also, prior retaining devices can be difficult to handle, install and/or manipulate.

There remains a need for instruments and methods that can be employed for efficiently and effectively preventing back-out of anchors relative to a bone plate and maintaining the engagement between the anchors and a bony segment.

SUMMARY

According to one aspect, a system involving a retaining mechanism for a bone plate is provided. The system includes a plate with at least a first hole therethrough between an upper surface and a lower surface of the plate to receive an anchor for engaging the plate to a bony segment. The plate includes at least one access bore adjacent the first hole and in communication with a first receptacle about the first hole. The system also includes a partially annular retaining member defining an aperture sized to allow passage of a bone engaging portion of the anchor therethrough. The retaining member is received in the first receptacle in a first configuration and is radially outwardly moveable in the first receptacle in response to passage of a head of the anchor therethrough. The retaining member returns toward the first configuration to engage the head of the anchor to block the anchor backing out of the first hole. Further, the retaining member is accessible through the access bore to radially move the retaining member to disengage the anchor.

Another aspect involves a method for retaining at least one bone engaging fastener relative to a bone plate. The method comprises inserting a partially annular retaining member in a first configuration into a first receptacle about a hole in the bone plate, with the hole extending between an upper surface and a lower surface of the bone plate. The bone plate includes at least one access bore adjacent the hole and in communication with the first receptacle. The method further comprises advancing the bone engaging fastener into the hole. The retaining member is moveable in a radially outwardly direction in the first receptacle in response to passage therethrough of a head of the bone engaging fastener. The retaining member returns toward the first configuration to engage the head of the bone engaging fastener and prevent the bone engaging fastener from backing out of the hole. The method further comprises accessing the retaining member through the at least one access bore to radially move the retaining member to disengage the bone engaging fastener.

Yet another aspect involves a system comprising a plate with at least a first hole therethrough between an upper surface and a lower surface of the plate. The first hole is configured to receive a first anchor for engaging the plate to a bony segment. The plate includes at least one receptacle in communication with the first hole. The receptacle opens toward an adjoining side surface to the upper and lower surfaces. The system further comprises an oblong retaining member being inserted in the receptacle in a first position. The retaining member is then movable to a second position to engage the first anchor and block the first anchor backing out of the first hole.

Even another aspect involves a system comprising a plate including at least a first hole therethrough extending along a central axis between an upper surface and a lower surface of the plate. The first hole is configured to receive an anchor for engaging the plate to a bony segment. The plate includes a first receptacle about the first hole and the anchor includes a second receptacle about a head of the anchor. The system further comprises a partially annular retaining member defining an aperture sized to allow passage of a bone engaging portion of the anchor therethrough. The retaining member is received in the first receptacle in a first configuration and is radially outwardly moveable in the first receptacle in response to passage of the head of the anchor therethrough. The retaining member is configured to return toward the first configuration to engage the head of the anchor at the second receptacle when the second receptacle aligns with the first receptacle. The first and second receptacles are sized relative to one another and the retaining member to allow the anchor in the first hole to toggle while the retaining member blocks the anchor backing out of the first hole.

Another aspect involves a method comprising providing a plate with at least a first hole therethrough between an upper surface and a lower surface of the plate and a first receptacle about the first hole. The method further comprises providing an anchor configured for receipt in the first hole to engage a bony segment. The anchor includes a second receptacle about a head of the anchor. The method further comprises inserting a partially annular retaining member in a first configuration into the first receptacle and advancing the anchor into the first hole. The retaining member is radially outwardly moveable in the first receptacle in response to passage therethrough of the head of the anchor. The retaining member returns toward the first configuration to engage the head of the anchor at the second receptacle to block the anchor backing out of the first hole. Additionally, the first and second receptacles are sized to allow the anchor to toggle in the first hole.

Yet another aspect involves a system comprising a plate with a first hole therethrough between an upper surface and a lower surface of the plate to receive an anchor for engaging the plate to a bony segment. The plate includes a bore adjacent the first hole and in communication with the first hole. The bore has an enlarged section adjacent the upper surface of the plate configured for receipt of a retaining element head and a reduced size section extending distally from the enlarged section configured for receipt of a retaining element tail. The bore has a support surface between the enlarged and reduced size sections. The system further includes a partially annular retaining member defining an aperture sized to allow passage of the tail of the retaining element therethrough. The retaining member is positioned between the support surface and the retaining element head in a first configuration and is moveable along the support surface in response to passage of a head of the anchor thereagainst. The retaining member returns toward the first configuration to overlap the first hole and block the anchor from backing out of the first hole.

Even another aspect involves a method comprising engaging a partially annular retaining member in a first configuration in a first bore in a bone plate with a retaining element. The bone plate includes a first hole adjacent the first bore and in communication with the first bore. The first hole extends between an upper surface and a lower surface of the plate. The method further comprises advancing an anchor into the second hole. The retaining member is radially inwardly moveable in the first hole in response to passage of a head of the anchor through the second hole. Further, the retaining member returns toward the first configuration to overlap the first hole and block the anchor backing out of the first hole.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Bone plates are engageable to bony segments with anchors. The bone plates are provided with retaining mechanisms configured relative to the plate holes to prevent backout of one or more anchors that engage the plate to the bony segment. The retaining mechanisms can either contact the bone anchor, overlap the plate hole through which the anchor extends, or both. The bone plates and anchor retaining systems can be employed in the stabilization of one or more levels of the spinal column in any approach to the spinal column, including anterior, antero-lateral, lateral, posterior approaches, and in any region of the spinal column, including the cervical, thoracic, lumbar, or sacral regions. Applications in addition to or other than spinal stabilization are also contemplated.

Figure 1:
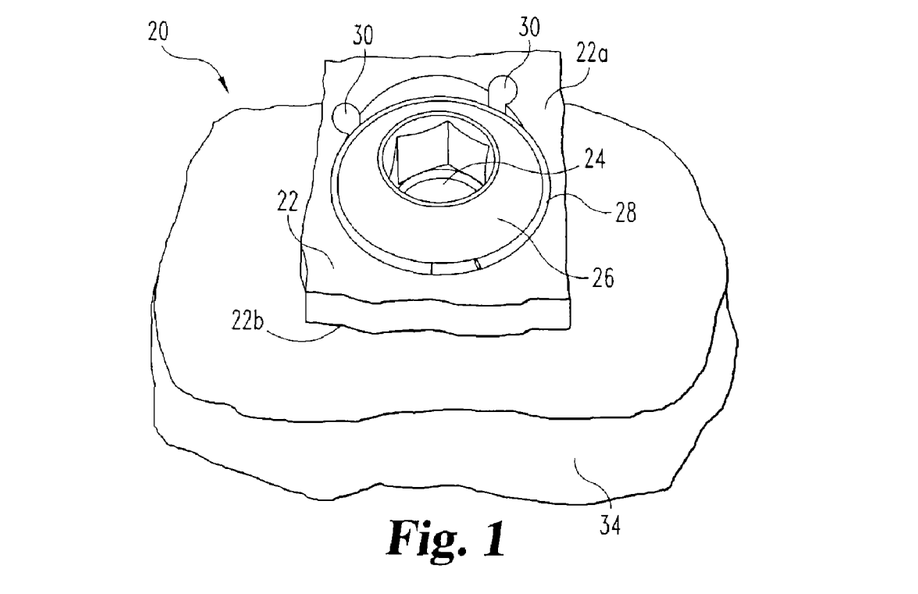
FIG. 1 is a schematic view of a portion of a plating system.
Figure 2:
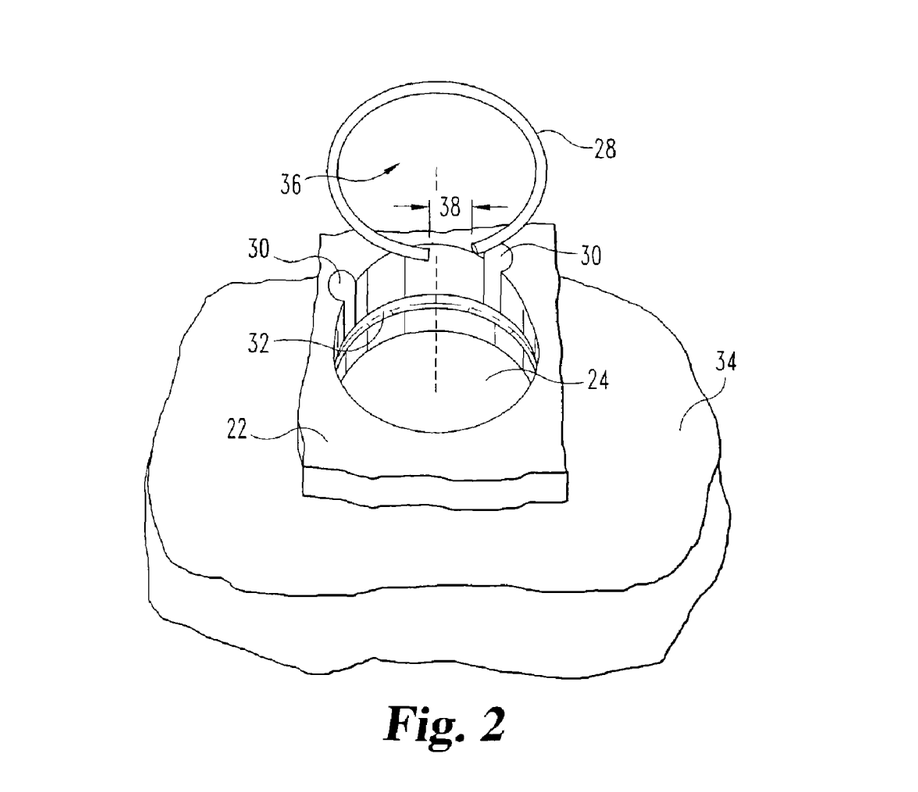
FIG. 2 is a partial, exploded, schematic view of the plating system of FIG. 1.

Referring to FIGS. 1 and 2, plating system 20 includes a bone plate 22 with at least one hole 24 for receiving an anchor 26 and a retaining member 28. Bone plate 22 is shown in partial view, but may include any suitable overall shape and form for plates for spinal stabilization, including plates employed for anterior, antero-lateral, lateral, and posterior stabilization procedures. Hole 24 extends between an upper surface 22$a$ and a lower surface 22$b$ of plate 22 and includes receptacle 32 thereabout for receipt of retaining member 28 therein. Access bores 30 are provided adjacent hole 24 and, in one embodiment, extend from upper surface 22$a$ of plate 22 to receptacle 32. Anchor 26 is positionable in hole 24 to secure plate 22 to bony structure 34 under plate 22. Retaining member 28 extends into hole 24 when anchor 26 is positioned in hole 24 and resists or blocks backout of anchor 26 from plate 22 and bony segment 34.

As illustrated, hole 24 can be generally circular; however, it should be appreciated that hole 24 can be configured or shaped differently in any manner suitable for receipt of an anchor. For example, hole 24 can be cylindrical, partially spherical, frusto-conical, and combinations thereof. As illustrated, receptacle 32 is in the form of a groove formed in plate 22 that extends completely about hole 24, although a groove that extends partially about hole 24 is also contemplated. Further, it should be appreciated that additional holes can be provided through bone plate 22, either in isolation, in adjacent hole pairs, or three or more adjacent holes. The plate discussed herein can be made from any one or a combination of suitable material, including metals and metal alloys, polymers, biological material, synthetic material, and resorbable material, for example.

Retaining member 28 is illustrated in the form of a C-shaped ring that has a generally circular cross-section and is partially annular in shape with respect to a plan view. However, other shapes for retaining member 28, including non-circular shapes, are contemplated. In the illustrated embodiment, retaining member 28 includes a central opening 36 therethrough and a gap 38 between two ends of retaining member 28. Central opening 36 is configured and sized for passage of at least a part of anchor 26 therethrough. Gap 38 allows for radial movement of retaining member 28 in response to forces applied thereto. In one embodiment, retaining member 28 is made from a resiliently deformable material having sufficient flexibility to bend, twist or otherwise move relative to receptacle 32 about hole 24 to assume any one of an infinite number of orientations with respect to plate 22. In another embodiment, retaining member 28 is fabricated from a plastic material having a rigidity that is less than that of the material comprising anchor 26. Thus, retaining member 28 can expand as anchor 26 is advanced therethrough during operation of system 20.

Figure 3:
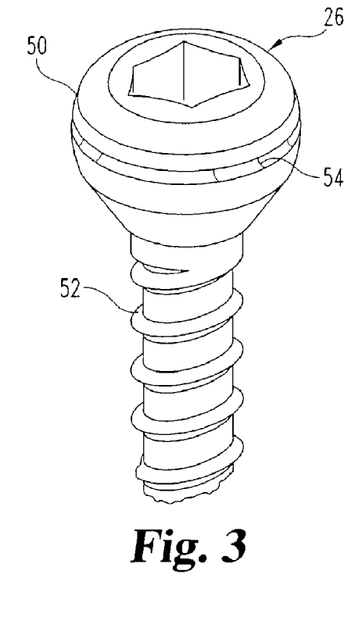
FIG. 3 is a partial, schematic view of an anchor of the plating system of FIG. 1.

Referring to FIG. 3, additional features of anchor 26 are shown. Anchor 26 includes a head 50 and a bone engaging portion, such as tail portion 52. In one embodiment, head 50 of anchor 26 can include a second receptacle 54 thereabout for at least partially receiving retaining member 28. Tail portion 52 can include a thread pattern therealong to engage bony structure 34. Tail portion 52 can be provided with a pointed or sharp leading end (not shown) to penetrate bony structure 34 underlying plate 22 or a blunt leading end. In the illustrated embodiment, tail portion 52 of anchor 26 includes a shaft structure with a generally cylindrical shape, although other shapes are also contemplated, including circular, square, rectangular, polygonal shape, and any other suitable shape for passage through hole 24 and engagement with bony structure 34. It should be appreciated that anchor 26 can be any type of bone engaging fastener, such as a screw, suture anchor, bolt, nail, staple, or other fastener capable of securing plate 22 to bony structure 34. When positioned in hole 24, head 50 of anchor 26 can be fixed, pivotal, translatable or otherwise movable in hole 24. It is contemplated that head 50 can extend at or at least slightly above upper surface 22a, or could be recessed below upper surface 22a.

Generally referring to FIGS. 1-3, use of system 20 by a surgeon may involve inserting retaining member 28 in either first receptacle 32 or second receptacle 54. Alternatively, retaining member 28 can be pre-assembled within receptacle 32 in plate 22, or retaining member 28 can be pre-assembled within receptacle 54 of anchor 26. This minimizes the fiddle factor to the surgeon during the procedure. Handling of plating system 20 is further facilitated since the retaining member 28 need not be moved, manipulated or otherwise handled during the procedure to obtain backout restraint for the inserted anchor. Plate 22 is positioned on bony structure 34 for engagement thereto with anchor 26. Anchor 26 is advanced into hole 24, with tail portion 52 of anchor 26 passing through retaining member 28, and at least a part of head 50 of anchor 26 passing through retaining member 28. Retaining member 28 is moveable relative to receptacle 32 in response to passage of anchor 26. In other words, as head portion 50 advances through hole 24 and retaining member 28, retaining member 28 expands radially outwardly into receptacle 32. The flexibility of retaining member 28 allows the ends between gap 38 to move away from one another during passage of anchor 26 through hole 24. Retaining member 28 thereafter resiliently returns toward its pre-insertion configuration, extending between head 50 of anchor 26 and plate 22.

As retaining member 28 returns toward its initial configuration, retaining member 28 is positioned in second receptacle 54 where it interferes with anchor 50 and prevents or substantially prevents axial movement of anchor 26 along hole 24. Retaining member 28 contacts head 50 in second receptacle 54, or can be spaced therefrom at any one of a number of positions thereabout, to secure anchor 26 to plate 22. In one embodiment, retaining member 28 is at least partially received in second receptacle 54 about head 50 to engage anchor 26. In the illustrated embodiment, receptacle 54 is a groove extending completely about head 50. Other embodiments contemplate that second receptacle 54 is formed by a groove extending partially about head 50, or by a stepped surface configuration that provides head 50 with a contact surface that is below retaining member 28 when anchor 26 is inserted into hole 24. In another embodiment, head 50 is provided without a second receptacle 54, and retaining member frictionally engages head 50.

After implantation and securement of plate 22 to the bony structure, retaining member 28 prevents and/or limits the backout of anchor 26 relative to plate 22. Specifically, the interference between retaining member 28 and head 50 blocks anchor 26 from backing out of hole 24 and out of engagement with bony structure 34. Additionally, in one embodiment, retaining member 28 can move relative to first receptacle 32 while maintaining contact with head 50 of anchor 26 to allow pivoting or toggling of anchor 26 in hole 22. It is also contemplated that retaining member 28 can be provided with sufficient flexibility to resiliently deform in response to movement of anchor 26, while maintaining contact with anchor 26. The movement of anchor 26 is limited when, for example, the resistance to further flexing, deformation and/or movement provided by retaining member 28 exceeds the backout force exerted by anchor 26.

Figure 4:
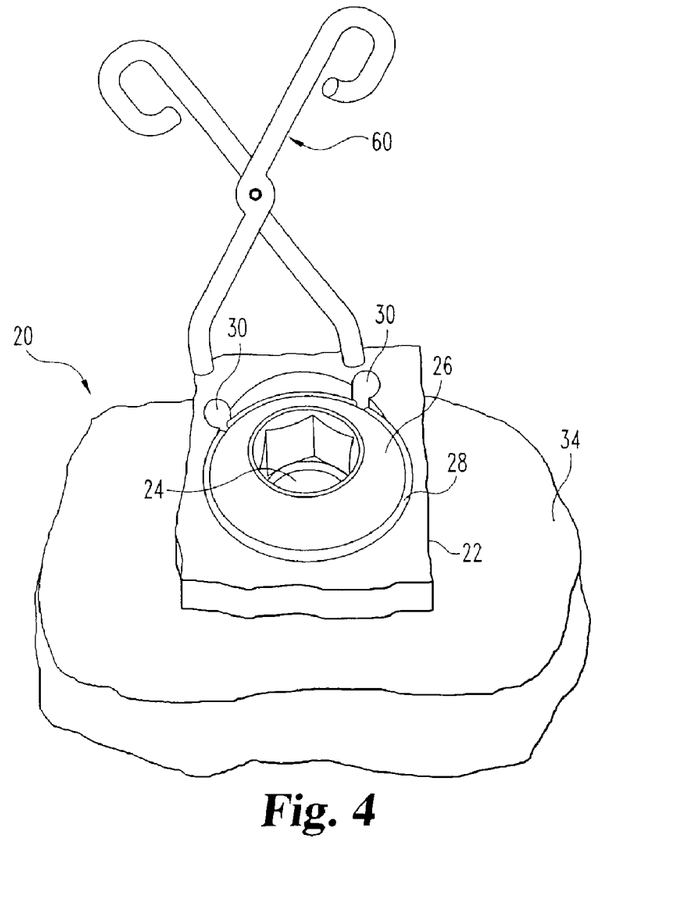
FIG. 4 is the plating system of FIG. 1 with a portion of a removal tool positioned adjacent thereto.

FIG. 4 illustrates plating system 20 and a tool 60 for removing anchor 26 from hole 24. Access bores 30 provide accessibility to the ends of retaining member 28 when at least one end of retaining member 28 is aligned with at least one of the access bores 30. In one embodiment, retaining member 28 can be radially expanded into receptacle 32 about hole 24 so that retaining member 28 is disengaged from or positioned out of second receptacle 54, allowing anchor 26 to be moved and/or removed from hole 24 as it is disengaged from bony structure 34. In one procedure, tool 60 can be inserted into access bores 30 to contact the ends of retaining member 28 to move the ends away from one another and radially outwardly expand retaining member 28. Tool 60 can be any appropriate tool for contacting and moving the ends of retaining member 28, such as tweezers, needle nose pliers, scissors, forceps, screw driver, or other tool, for example.

Figure 5A:
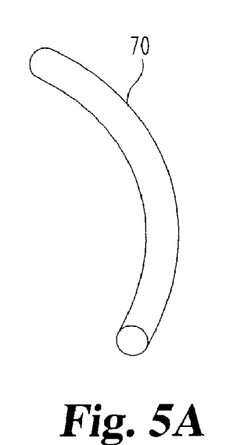
FIG. 5A is a partial, schematic view of a portion of one embodiment retaining member of the plating system of FIG. 1.
Figure 5B:
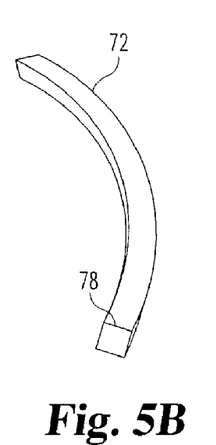
FIG. 5B is a partial, schematic view of a portion of another embodiment retaining member of the plating system of FIG. 1.
Figure 5C:
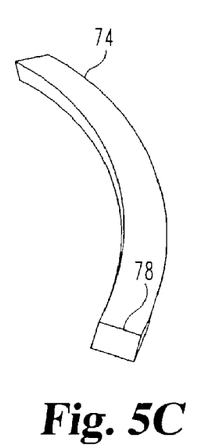
FIG. 5C is a partial, schematic view of a portion of another embodiment retaining member of the plating system of FIG. 1.
Figure 5D:
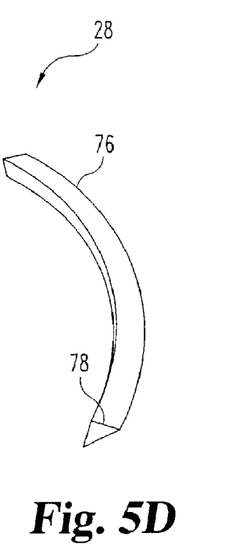
FIG. 5D is a partial, schematic view of a portion of another embodiment retaining member of the plating system of FIG. 1.

FIGS. 5A-5D illustrate various embodiments of retaining member 28 incorporating various cross-sectional shapes. For example, in FIG. 5A retaining member 70 has a generally circular cross-sectional shape. Other embodiments contemplate that an upper surface of the retaining member includes a non-circular shape that contacts the adjacent surface of first receptacle 32 to facilitate or enhance resistance to anchor backout. For example, in FIG. 5B retaining member 72 has a generally square cross-sectional shape. In FIG. 5C, retaining member 74 has a generally rectangular cross-sectional shape. In FIG. 5D, retaining member 76 has a generally triangular cross-sectional shape. In the embodiments of FIGS. 5B-5D, each retaining member includes cross-section with at least an upper surface 78 that is non-circular or non-curved in shape. Other embodiments contemplate even other shapes, including polygonal or non-circular cross-sectional shapes.

Figure 6:
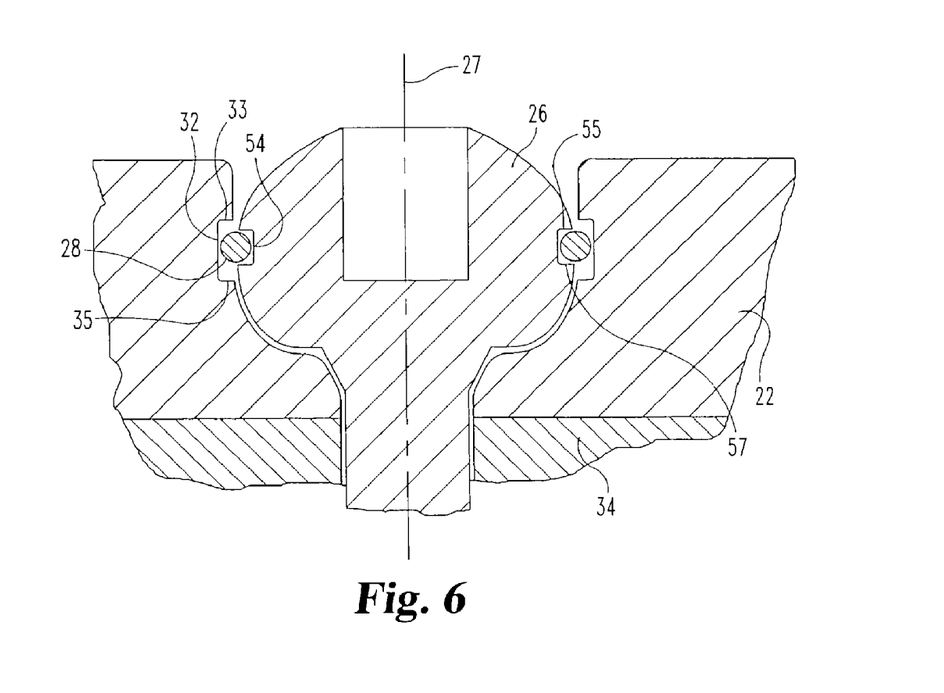
FIG. 6 is a partial, sectional, schematic view of the plating system of FIG. 1.

Retaining member 28 can be used with bone plates and anchors in which the anchors are fixed relative to the plate to prevent or limit the backout of the fixed anchors from the plate. Retaining member 28 can also be used with bone plates and anchors in which pivoting and/or translation of the anchors relative to the plate is desirable while preventing or limiting the backout of the anchors from the plate, as illustrated in FIG. 6. Additionally, the same retaining member 28, or multiple retaining members 28, can also be employed with any one or a combination of fixed, pivotal, and translatable anchors in the same bone plate.

FIG. 6 is a cross-sectional illustration of one embodiment connection relationship between plate 22, anchor 26 and retaining mechanism 28. As illustrated, first receptacle 32 and second receptacle 54 are sized relative to one another and also relative to retaining member 28 to allow anchor 26 to pivot or toggle while engaged to bony structure 34, providing a variable angle relationship therewith. This allows anchor 26 to move with bony structure 34 while engaged with plate 22, and also provides different placement angles for anchor 26 through plate 22. In the illustrated embodiment, first receptacle 32 has a greater height along central axis 27 of hole 24 than the height of second receptacle 54 along central axis 27 of hole 24. The difference in heights of the receptacles 32 and 54 allows anchor 26 to move within hole 24; however, the movement can be limited at positions where retaining member 28 contacts upper and lower surfaces 33, 35 of first receptacle 32. Retaining member 28 has a height that provides a close fit between upper and lower surfaces 55, 57 of second receptacle 54. The heights of first receptacle 32 and second receptacle 54 can be varied relative to one another to allow for various degrees of angular movement, while still maintaining the functional integrity of retaining member 28. In still another embodiment, second receptacle 54 is provided with a greater height than first receptacle 32.

Figure 7:
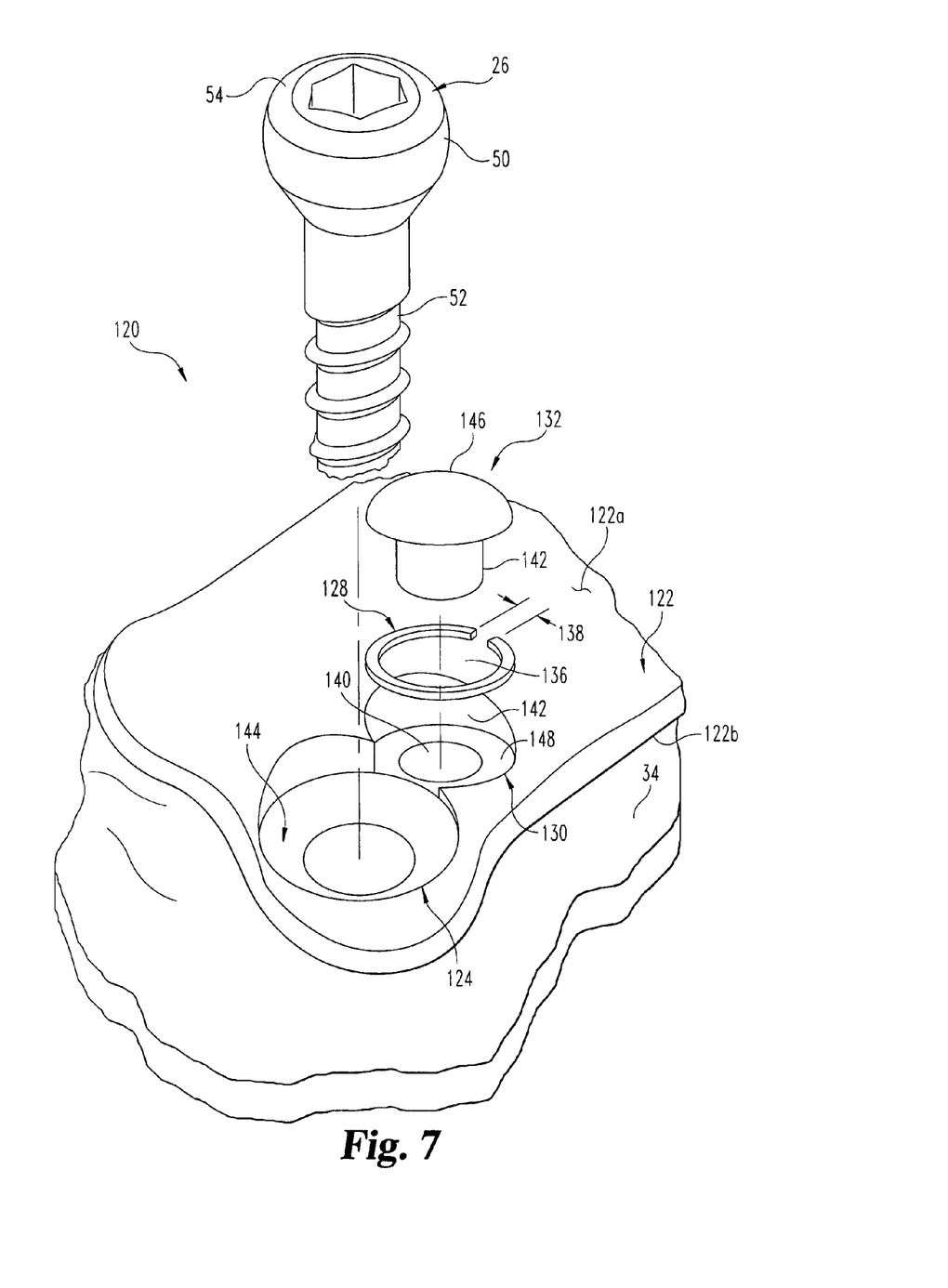
FIG. 7 is a partial, exploded, schematic view of another embodiment plating system.

Referring to FIG. 7, another embodiment plating system 120 is illustrated. Reference numerals that refer to like features previously described in connection with system 20 are similarly designated. Plating system 120 includes bone plate 122 with first hole 124, anchor 26, retaining member 128, a first bore 130, and retaining element 132. Similar to system 20, anchor 26 is positionable in hole 124 to secure plate 122 to bony structure 34 under plate 122. First hole 124 extends between an upper surface 122a and a lower surface 122b of plate 122.

First bore 130 is configured for receipt of retaining element 132 and includes a reduced size section 140 for receipt of tail portion 142 of retaining element 132, and an enlarged section 144 for receipt of head portion 146 of retaining element 132. The transition between enlarged section 144 and reduced size section 140 defines a support surface 148 upon which or adjacent which retaining member 128 is positioned. First hole 124 and first bore 130 overlap and are in communication with each other. When assembled, at least a portion of retaining member 128 projects into and overlaps hole 124 so that an anchor seated in hole 124 will be contacted or blocked from backing out of the hole by retaining member 128.

Additionally or alternatively, lower surface 122b of plate 122 can include a countersink (not shown) extending about first bore 130 to assist in securing retaining element 132 in first bore 130. It should be appreciated that additional anchor holes can be provided through bone plate 122, either in isolation, in adjacent hole pairs, or three or more adjacent holes. For example, numerous holes can surround one central bore configured for receipt of a retaining member and a retaining element, and the anchors inserted in the numerous holes can be retained by the one central retaining member and retaining element. Alternatively, a single retaining member can be provided for each one of or for each hole of a subset of the holes of the plate.

In use, system 120 includes positioning retaining member 128 into enlarged section 144 of bore 130 and onto or adjacent to support surface 148. Alternatively, retaining member 128 can be pre-assembled within bore 130 with retaining element 132 engaged in reduced size section 140 of plate 122. Plate 122 is positioned on bony structure 34 for engagement thereto with anchor 26 advanced into hole 124. In one embodiment, anchor 26 is rotated so that tail portion 52 threadingly engages bony structure 34. Retaining member 128 is moveable relative to support surface 148 of bore 130 in response to passage of anchor 26 thereagainst so that hole 24 is at least temporarily unobstructed by retaining member 128. As anchor 26 advances through hole 124, the spherical underside of head 50 acts on retaining member 128 so it can move away from hole 124 or contract radially inwardly. The flexibility of retaining member 128 allows retaining member 128 to return toward its pre-insertion configuration in overlapping relation with hole 124.

After anchor 26 is inserted and seated in hole 124, retaining member 128 resiliently returns toward an initial configuration to constrain or limit backout of anchor 26. In one embodiment, when retaining member 128 returns toward an initial configuration, retaining member 128 partially occupies space in hole 124 above anchor 26, thereby blocking anchor 26 backing out of hole 124. Retaining member 128 can be positioned in abutting contact with an upper surface of head 50 of anchor 26, or can normally be spaced from head 50 and contact head 50 only upon backout of anchor 50. Other embodiments contemplate that retaining member 128 is engageable to head 50 of anchor 26 at any one of a number of positions to secure anchor 26 to plate 122 and bony structure 34. It is still further contemplated that head 50 can be provided with a receptacle to receive retaining member 128, or that head 50 can be provided without any receptacle as shown in FIG. 7.

Retaining member 128 is illustrated in the form of a C-shaped ring and includes a central opening 136 and a gap 138 between the ends of retaining member 128. Retaining member 128 can be configured similarly to retaining member 28; however, retaining member 128 does not receive tail portion 52 of anchor 26. Rather, tail portion 142 of retaining element 132 can be positioned or received through central opening 136. A non-circular lower surface of retaining member 128 can be provided to contact head 50, either upon insertion or in response to backout of anchor 26, to increase resistance against anchor 26 backing out. Additionally, in one embodiment, anchor 26 includes a head 50 having a flattened upper surface portion 54 that contacts retaining member 128 to further increase resistance to thus better prevent or block anchor 26 backing out of hole 124.

When retaining member 128 has returned toward an initial configuration to block backout of anchor 26, retaining element 132 can be advanced into bore 130 to maintain positioning of retaining member 128 and secure it within bore 130. Retaining element 132 is advanced into bore 130 with tail portion 142 received in reduced size section 140 and head portion 146 received in enlarged section 144. Head portion 146 of retaining element 132 is operable to constrain retaining member 128 on support surface 148 within bore 130. In another embodiment, retaining element 132 is pre-engaged, captured, or formed on plate 122 to maintain retaining member 128 on plate 122 yet allow retaining member to move in response to passage of anchor 26 thereby. This allows the retaining member 128 to be pre-assembled with plate 122, and minimizes the fiddle factor to the surgeon during the procedure. Handling of plating system 120 is further facilitated since the retaining member 128 need not be moved, manipulated or otherwise handled during the procedure.

Retaining member 128 can also be manipulated to enable removal of anchor 26 from hole 124. Retaining member 128 can be radially contracted along support surface 148 of bore 130. When retaining member 128 is positioned so as to not occupy space within hole 124, anchor 26 can be moved and/or removed from hole 124 and disengaged from bony structure 34. In one embodiment, a tool can be inserted into hole 124 adjacent upper surface 122a of plate 122 to contact and radially contract or move retaining member 128. The tool used to move retaining member 128 can be any appropriate tool to move retaining member 128 out of the path of hole 124. Thereafter, a screwdriver or other such tool or device can be utilized to remove anchor 26 from hole 124.

Figure 8:
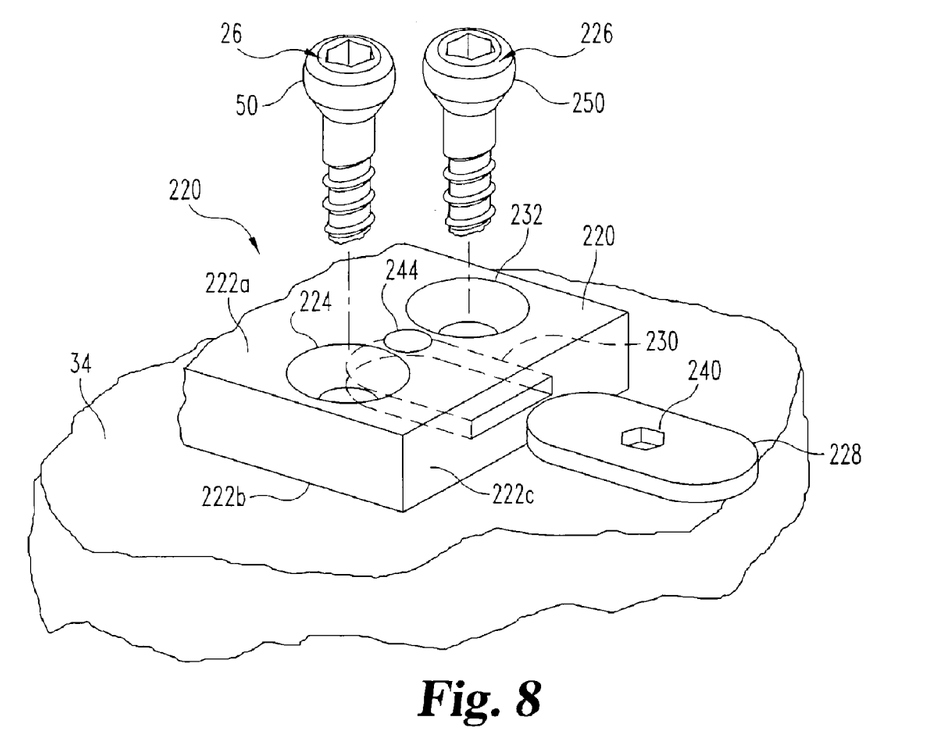
FIG. 8 is a partial, exploded, schematic view of another embodiment plating system.

FIG. 8 illustrates another embodiment plating system 220, and like reference numerals refer to like features previously described in connection with systems 20 and 120. Plating system 220 includes bone plate 222 with first hole 224 for receiving anchor 26. As illustrated, bone plate 222 can also include a second hole 232 for receiving anchor 226. Holes 224, 232 extend between an upper surface 222a and a lower surface 222b of plate 222. First anchor 26 and second anchor 226 are positionable in first hole 224 and second hole 232, respectively, to secure plate 222 to bony structure 34 under plate 222. Plate 222 further includes receptacle 230 configured for receipt of retaining member 228.

In one embodiment, receptacle 230 extends from an adjoining side surface 222c of plate 222 to holes 224 and 232. In one embodiment, receptacle 230 extends between and is communication with holes 224 and 232, and receptacle 230 opens into both holes 224 and 232. Retaining member 228 is received in receptacle 230 and is positionable in contact with head 50 of anchor 26 and head 250 of anchor 226 positioned in plate 222 to resist backout of anchors 26, 226 from plate 222 and bony segment 34.

Figure 9:
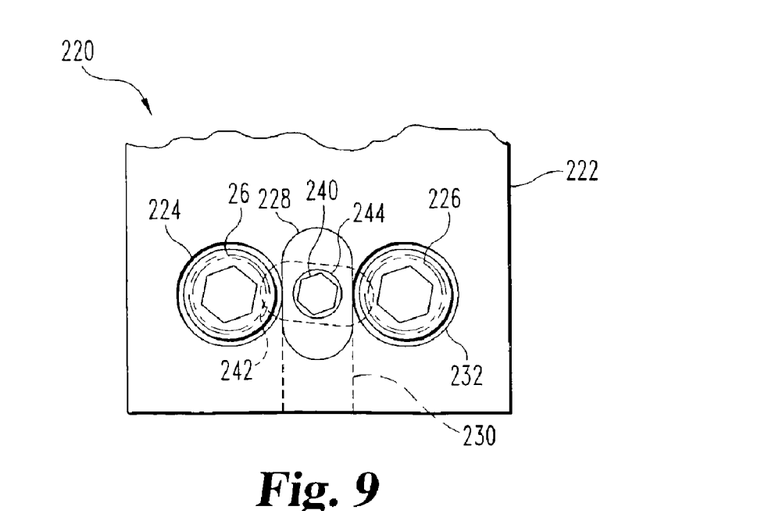
FIG. 9 is a partial, schematic top plan view of the plating system of FIG. 8.

In use, retaining member 228 can be inserted in receptacle 230, as illustrated in FIG. 9. Alternatively, retaining member 228 can be pre-assembled within receptacle 230 of plate 222. Plate 222 is positioned on bony structure 34 for engagement thereto either before or after retaining member 228 is received in receptacle 230. First and second anchors 26, 226 are inserted in first and second holes 224, 232, respectively, to engage plate 222 to bony structure 34. It is contemplated that anchors 26, 226 can be inserted into holes 224, 232, respectively, before positioning of retaining member 228 so that it extends into holes 224, 232. When retaining member 228 is inserted in receptacle 230, a tool receiving portion 240 of retaining member 228 is accessible through opening 244 in upper surface 222a of plate 222. After insertion of first and second anchors 26, 226 in first and second holes 224, 232, respectively, retaining member 228 can be moved to second position 242 shown in FIG. 9 by inserting a tool through opening 244 into tool receiving portion 240 and rotating retaining member 228 to second position 242. In second position 242, retaining member 228 contacts the heads 50, 250 of anchors 26, 226 and prevents or substantially prevents first and second anchors 26, 226 from backing out of the respective plate holes.

In the illustrated embodiment, retaining member 228 has a generally oblong shape to facilitate engagement of anchors 26, 226 when retaining member 228 is at second position 242. However, it should be appreciated that retaining member 228 can include any shape, including rectangular, oval, cross, star, diamond, or polygonal shapes, for example.

Retaining member 228 is rotated to engage anchors 26, 226 to simultaneously block anchors 26, 226 from backing out of holes 224, 232, respectively. Retaining member 228 is generally positionable in contact with an upper surface or receptacle in head 50 of anchor 26 and head 250 of anchor 226 at any one of a number of positions. In one embodiment, head 50 of anchor 26 and head 250 of anchor 226 are recessed below upper surface 222a of plate 222, and second position 242 of retaining member 228 is above heads 50, 250 of anchors 26, 226, respectively. In another embodiment, retaining member 228 is positioned in receptacles in heads 50, 250 of anchors 26, 226 when in second position 242. It is contemplated that retaining member 228 can be provided rigid in form or with sufficient flexibility to resiliently move and deform to contact and in response to movement of anchors 26 and 226, while maintaining contact with anchors 26, 226.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal plating system, comprising:
   a plate including at least a first hole therethrough between an upper surface and a lower surface of said plate to receive an anchor for engaging said plate to a bony segment, said plate including first and second access bores adjacent said first hole in communication with a first receptacle about said first hole; and
   a partially annular retaining member defining an aperture sized to allow passage of a bone engaging portion of said anchor therethrough, wherein said retaining member is received in said first receptacle in a first configuration and is radially outwardly moveable in said first receptacle in response to passage of a head of said anchor therethrough, wherein said retaining member returns toward said first configuration to engage said head of said anchor and prevent said anchor from backing out of said first hole, wherein said retaining member includes opposing first and second ends aligned with respective ones of said first and second access bores, said first and second ends being simultaneously accessible through said first and second access bores to radially outwardly move said retaining member to disengage said anchor.

2. The system of claim 1, wherein said access bore extends from said upper surface of said plate to said first receptacle.

3. The system of claim 1, wherein in operation said first and second ends of said retaining member are moved away from one another radially outwardly move said retaining member to disengage said retaining member from said anchor.

4. The system of claim 1, wherein said retaining member includes a non-circular surface extending thereabout, said surface being proximate to said upper surface of said plate and spaced away from said anchor.

5. The system of claim 1, wherein said first and second ends of said retaining member form a gap therebetween.

6. The system of claim 1, wherein said anchor includes a second receptacle thereabout for at least partially receiving said retaining member when said retaining member engages said head of said anchor.

7. The system of claim 6, wherein said first receptacle and said second receptacle are sized relative to said retaining member to allow said anchor in said first hole to toggle with said retaining member in said first and second receptacles.

8. The system of claim 7, wherein said first receptacle has a height along said hole that is greater than a height of said second receptacle along said head of said anchor.

9. The system of claim 1, wherein said first and second access bores are sized for receipt of a tool to contact said first and second nds of said retaining member to radially outwardly expand said retaining member to disengage said anchor.

10. The system of claim 9, wherein in operation said tool moves said retaining member into said first receptacle and out of a second receptacle about said head of said anchor to remove said anchor from said first hole.

11. A spinal system, comprising:
    a plate including at least a first hole therethrough extending along a central axis between an upper surface and a lower surface of said plate to receive an anchor for engaging said plate to a bony segment, said plate including a first receptacle about said first hole, said anchor including a second receptacle about a head of said anchor; and
    a partially annular retaining member defining an aperture sized to allow passage of a bone engaging portion of said anchor therethrough, said retaining member being received in said first receptacle in a first configuration and being radially outwardly moveable in said first receptacle in response to passage of said head of said anchor therethrough, said retaining member being configured to return toward said first configuration to engage said head of said anchor at said second receptacle when said second receptacle aligns with said retaining member, wherein said first receptacle and said second receptacle are sized relative to said retaining member to allow said anchor to toggle in said first hole while said retaining member blocks said anchor from backing out of said first hole.

12. The system of claim 11, wherein said first receptacle has a height along said central axis that is greater than a height of said second receptacle.

13. The system of claim 12, wherein said retaining member includes a height that substantially corresponds to a height of said second receptacle.

14. The system of claim 11, wherein said plate further includes at least one access bore adjacent said first hole in communication with said first receptacle, said retaining member being accessible through said bore to be radially outwardly expanded to disengage said anchor.

15. The system of claim 11, wherein:
said plate includes first and second access bores adjacent said first hole in communication with said first receptacle about said first hole; and
said retaining member includes opposing first and second ends aligned with respective ones of said first and second access bores, said first and second ends being simultaneously accessible through said first and second access bores to radially outwardly move said retaining member in said receptacle to disengage said anchor.

* * * * *